US00PP28858P2

(12) United States Plant Patent
Wood

(10) Patent No.: US PP28,858 P2
(45) Date of Patent: Jan. 9, 2018

(54) ***HYDRANGEA* PLANT NAMED 'SMNHALR'**

(50) Latin Name: *Hydrangea arborescens*
Varietal Denomination: SMNHALR

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 14/121,373

(22) Filed: Aug. 26, 2014

(51) Int. Cl.
*A01H 5/02* (2006.01)

(52) U.S. Cl.
USPC ..... Plt./250

(58) Field of Classification Search
USPC ..... Plt./250
CPC ..... A01H 5/02; A01H 5/00
See application file for complete search history.

(56) References Cited

PUBLICATIONS http://www.shopyourway.com/hirts-trees-shrubs-hydrangea-lime-rickey-smooth-hydrangea-4-pot-hydrangea-arborescens-smnhalr-ppaf-c/425269917; 2014; 3 pages.*

* cited by examiner

*Primary Examiner* — Kent L Bell
(74) *Attorney, Agent, or Firm* — C. A. Whealy

(57) ABSTRACT

A new and distinct cultivar of *Hydrangea* plant named 'SMNHALR', characterized by its upright, outwardly spreading and mounded plant habit; strong and sturdy stems; dark green-colored leaves; large mophead-type inflorescences with light green-colored sterile flowers; and good garden performance.

2 Drawing Sheets

Botanical designation: *Hydrangea arborescens.*
Cultivar denomination: 'SMNHALR'.

BACKGROUND OF THE INVENTION

The present invention relates to a new and distinct *Hydrangea* plant, botanically known as *Hydrangea arborescens* and hereinafter referred to by the name 'SMNHALR'.

The new *Hydrangea* plant is a product of a planned breeding program conducted by the Inventor in Grand Haven, Mich. The objective of the breeding program was to develop new *Hydrangea* plants with strong stems and large attractive inflorescences.

The new *Hydrangea* plant originated from a cross-pollination conducted by the Inventor in July, 2007 of an unnamed selection of *Hydrangea arborescens radiata*, not patented, as the female, or seed parent and *Hydrangea arborescens* 'Pink Pincushion', not patented, as the male, or pollen, parent. The new *Hydrangea* plant was discovered and selected by the Inventor as a single flowering plant from within the progeny of the stated cross-pollination in a controlled environment in Grand Haven, Mich. in July, 2011.

Asexual reproduction of the new *Hydrangea* plant by softwood cuttings in a controlled environment in Grand Haven, Mich. since July, 2011 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNHALR'. These characteristics in combination distinguish 'SMNHALR' as a new and distinct *Hydrangea* plant:

1. Upright, outwardly spreading and mounded plant habit.
2. Strong and sturdy stems.
3. Dark green-colored leaves.
4. Large mophead-type inflorescences with light green-colored sterile flowers.
5. Good garden performance.

Plants of the new *Hydrangea* differ from plants of the female parent selection primarily in sterile flower color as plants of the female parent selection have white-colored sterile flowers.

Plants of the new *Hydrangea* differ from plants of the male parent, 'Pink Pincushion', in the following characteristics:

1. Plants of the new *Hydrangea* have larger inflorescences than plants of 'Pink Pincushion'.
2. Sterile flowers of plants of the new *Hydrangea* are light green in color whereas sterile flowers of plants of 'Pink Pincushion' are pink in color.

Plants of the new *Hydrangea* can be compared to plants of *Hydrangea arborescens* 'Annabelle', not patented. In side-by-side comparisons, plants of the new *Hydrangea* differed primarily from plants of 'Annabelle' in the following characteristics:

1. Plants of the new *Hydrangea* were taller than plants of 'Annabelle'.

2. Sterile flowers of plants of the new *Hydrangea* were light green in color whereas sterile flowers of plants of 'Annabelle' were white in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a top perspective view of a typical plant of 'SMNHALR' grown in an outdoor nursery.

The photograph on the second sheet is a close-up view of a typical flowering plant of 'SMNHALR'.

DETAILED BOTANICAL DESCRIPTION

Plants used for the aforementioned photographs and the following description were grown during the summer in three-gallon containers and in ground beds in an outdoor nursery in Grand Haven, Mich. and under cultural practices typical of commercial *Hydrangea* production. Plants of the new *Hydrangea* were three years old when the photographs and description were taken. In the following description, color references are made to The Royal Horticultural Society Colour Chart, 1995 Edition, except where general terms of ordinary dictionary significance are used.

Botanical description: *Hydrangea arborescens* 'SMNHALR'.

Parentage:

*Female, or seed, parent*.—Unnamed selection of *Hydrangea arborescens radiata*, not patented.

*Male, or pollen, parent*.—*Hydrangea arborescens* 'Pink Pincushion', not patented.

Propagation:

*Type cutting*.—By softwood cuttings.

*Time to initiate roots, summer*.—About 18 days at temperatures about 27° C.

*Time to produce a rooted young plant, summer*.—About 60 days at temperatures about 27° C.

*Root description*.—Fine to thick; white and brown in color.

*Rooting habit*.—Freely branching; dense.

Plant description:

*Plant form and growth habit*.—Perennial deciduous shrub; upright, outwardly spreading and mounded plant habit; inverted triangle; strong and sturdy lateral branches; freely branching habit with about 61 to 100 lateral branches developing per plant; vigorous growth habit.

*Plant height*.—About 100 cm.

*Plant diameter or area of spread*.—About 50 cm.

*Lateral branches*.—Length: About 67 cm. Diameter: About 5 mm. Internode length: About 7 cm. Texture: Smooth, glabrous. Strength: Strong, sturdy. Aspect: Mostly upright. Color: Close to 146C.

Leaf description:

*Arrangement*.—Opposite, simple.

*Length*.—About 8 cm to 16 cm.

*Width*.—About 5 cm to 12 cm.

*Shape*.—Cordate.

*Apex*.—Acute to acuminate.

*Base*.—Obtuse.

*Margin*.—Serrate.

*Texture, upper surface*.—Slightly rough; pubescent.

*Texture, lower surface*.—Slightly rough and ribbed; slightly pubescent.

*Venation pattern*.—Pinnate.

*Color*.—Developing and fully expanded leaves, upper surface: Close to 139A; venation, close to 145A. Developing and fully expanded leaves, lower surface: Close to 137C; venation, close to 145C.

*Petioles*.—Length: About 6 cm. Diameter: About 2 mm. Texture, upper and lower surfaces: Pubescent. Color, upper surface: Close to 145A overlain with close to 177A. Color, lower surface: Close to 145A.

Flower description:

*Flower type and habit*.—Single sterile and fertile flowers arranged on terminal mophead cymes that are roughly hemispherical in shape; flowers face upright to outwardly.

*Fragrance*.—None detected.

*Natural flowering season*.—Plants flower from late spring to early summer in Grand Haven, Mich.; flowers persistent.

*Quantity of flowers*.—Freely flowering habit; about 560 fertile flowers and about 805 sterile flowers developing per inflorescence.

*Inflorescence height*.—About 15 cm.

*Inflorescence diameter*.—About 20 cm.

*Flower diameter, fertile flowers*.—About 6 mm.

*Flower depth (height), fertile flowers*.—About 5 mm.

*Flower diameter, sterile flowers*.—About 1.5 cm.

*Flower depth (height), sterile flowers*.—About 7 mm.

*Flower buds, fertile and sterile flowers*.—Length: About 3 mm. Diameter: About 2 mm. Shape: Obovate. Color: Close to 145C overlain with close to 186A.

*Petals, fertile flowers*.—Quantity and arrangement: About five in a single whorl. Length: About 2 mm. Width: About 1 mm. Shape: Ovate. Apex: Acute. Base: Obtuse. Margin: Entire. Texture, upper and lower surfaces: Smooth, glabrous. Color: When opening, upper and lower surfaces: Close to 186A becoming closer to 145A with development. Fully opened, upper and lower surfaces: Close to 155B becoming closer to 145A with development.

*Sepals, fertile flowers*.—If present, too small to measure; inconspicuous.

*Petals, sterile flowers*.—Quantity and arrangement: About four in a single whorl. Length: About 1 mm. Width: About 0.5 mm. Shape: Ovate. Apex: Acute. Base: Rounded to obtuse. Margin: Entire. Texture, upper and lower surfaces: Smooth, glabrous. Color: When opening, upper and lower surfaces: Close to 145C overlain with close to 186A. Fully opened, upper and lower surfaces: Close to 155B becoming closer to 144A with development.

*Sepals, sterile flowers*.—Quantity and arrangement: About four in a single whorl. Length: About 7 mm. Width: About 7 mm. Shape: Ovate. Apex: Acute. Base: Obtuse. Margin: Entire. Texture, upper and lower surfaces: Smooth, glabrous. Color: When opening, upper surface: Close to 144A. When opening, lower surface: Close to 145A. Fully opened, upper surface: Close to 155B becoming closer to 144A with development. Fully opened, lower surface: Close to 155B becoming closer to 145A with development.

*Pedicels, fertile flowers*.—Aspect: Upright to outwardly. Strength: Strong, sturdy. Length: About 1.5 mm. Diameter: About 1 mm. Texture: Smooth. Color: Close to 145A.

*Pedicels, sterile flowers*.—Aspect: Upright to outwardly. Strength: Strong, sturdy. Length: About 7 mm. Diameter: About 1 mm. Texture: Smooth. Color: Close to 145A.

*Reproductive organs, fertile flowers*.—Stamens: Quantity per flower: About ten. Filament length: About 1 mm. Filament color: Close to 155A. Anther shape: Round. Anther length: About 1 mm. Anther color: Close to 186A. Pollen amount: Scarce. Pollen color: Close to 155A. Pistils: Pistil quantity per flower: One; two to three-lobed. Pistil length: About 1 mm to 2 mm. Stigma shape: Round. Stigma color: Close to 155A. Style length: About 1 mm. Style color: Close to 155A.

*Reproductive organs, sterile flowers*.—Stamens: Quantity per flower: About six to eight. Filament length: About 2 mm. Filament color: Close to 155A. Anther shape: Round. Anther length: About 1 mm. Anther color: Close to 186A. Pollen amount: Scarce. Pollen color: Close to 155A. Pistils: Not observed on sterile flowers.

*Seeds, observed on fertile flowers only*.—Quantity per inflorescence: Numerous. Size: Less than 0.1 mm by less than 0.1 mm; dust-like. Color: Brown.

Disease & pest resistance: Plants of the new *Hydrangea* have not been observed to be resistant to pathogens and pests common to *Hydrangea* plants.

Garden performance: Plants of the new *Hydrangea* have been shown to exhibit good garden performance and to resist sun-scalding. Plants of the new *Hydrangea* have been observed to tolerate temperatures ranging from about −32° C. to about 36° C.

It is claimed:

1. A new and distinct *Hydrangea* plant named 'SMNHALR' as illustrated and described.

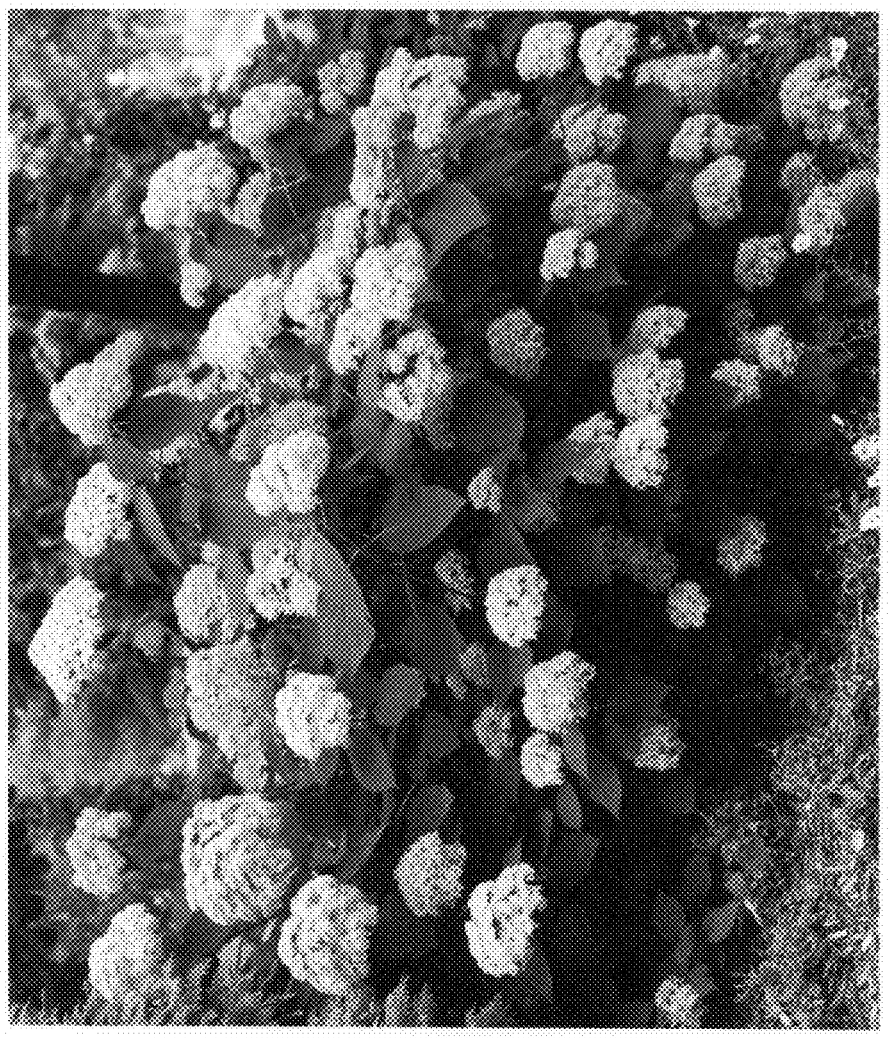

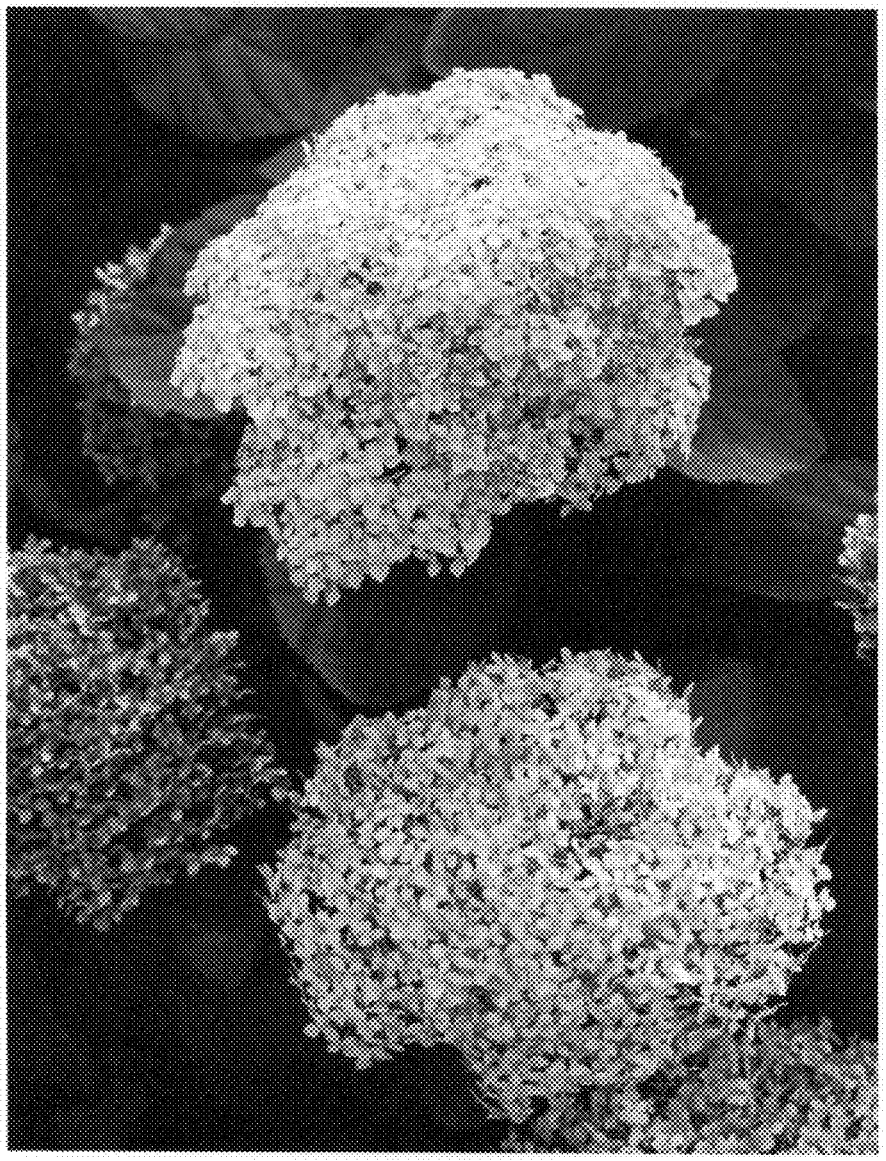

* * * * *